United States Patent [19]

Guerineau et al.

[11] Patent Number: 5,360,517
[45] Date of Patent: Nov. 1, 1994

[54] BACTERIAL DISINFECTION OF FLORA-CONTAMINATED PAPERMAKING PROCESS STREAMS

[75] Inventors: Pierre Guerineau, Biard, France; Peter Rosli, Mullingen, Switzerland

[73] Assignee: Texel, Dange Saint Romain, France

[21] Appl. No.: 21,668

[22] Filed: Feb. 24, 1993

[30] Foreign Application Priority Data

Feb. 24, 1992 [FR] France .................. 92 02080

[51] Int. Cl.⁵ .......................... D21F 1/66; B08B 3/00; C02F 3/34
[52] U.S. Cl. .................... 162/161; 210/611; 210/764; 435/882
[58] Field of Search ............. 210/611, 764, 765, 928; 162/161; 435/277, 278, 882

[56] References Cited

U.S. PATENT DOCUMENTS

| | | | |
|---|---|---|---|
| 3,658,700 | 4/1972 | Lederer | 162/161 |
| 3,981,766 | 9/1976 | Pechhold | 162/161 |
| 5,128,051 | 7/1992 | Theis et al. | 210/764 |
| 5,162,221 | 11/1992 | Brockamp et al. | 435/882 |
| 5,242,593 | 9/1993 | Oberkofler et al. | 210/611 |

FOREIGN PATENT DOCUMENTS

0372520A2  6/1990  European Pat. Off. .

*Primary Examiner*—Thomas Wyse
*Attorney, Agent, or Firm*—Burns, Doane, Swecker & Mathis

[57] ABSTRACT

Bacteria of the genus *Staphylococcus* or *Acinetobacter* are used in effective disinfectant amounts to regulate the growth of the microbial/bacterial flora existing in aqueous papermaking circuits/process streams, notably bacteria of the species *Staphylococcus carnosus*.

6 Claims, No Drawings

BACTERIAL DISINFECTION OF FLORA-CONTAMINATED PAPERMAKING PROCESS STREAMS

BACKGROUND OF THE INVENTION

1. Field of the Invention

The present invention relates to a process for regulating the growth of the microbial and/or bacterial flora, yeasts, molds and enterobacteria, that grow and flourish in the water circuits or processing streams in the papermaking industry.

2. Description of the Prior Art

Used paper and paperboard, generally designated "cellulosic recovery fibers," are today, as is wood, important raw materials in the papermaking industry. The recycling of such fibers is generally carried out in paper mills according to the following sequence:

The paper and fiberboard, recovered and stripped of any foreign body of the staple or plastics type, for example, are introduced into a pulper or disintegrator and therein dispersed in water. The resulting pulp, comminuted and then deflaked, is then subjected to a refining step, entailing swelling the cellulosic fibers by hydration. The actual production with initial formation of a sheet of paper is subsequently carried out on a filter cloth or wire with removal of water, drying and finally winding.

The paper production line hence includes a continuous water feed, the water being partially recycled, generally via a plurality of ancillary water circulation circuits.

The partial recycling of this water in the production line naturally promotes the growth of bacterial flora. This flora is undesirable since it causes slime formation.

In the papermaking industry, "slimes" are the chemical or biological deposits that occur in the production circuit. They can comprise fibers, carbonates or other inorganic fillers or bacteria. Upon detachment from the tanks or pipes in which they have accumulated, these slimes cause breaks in the paper and colored spots thereon. This results in frequent halts in the production line and a deterioration in working conditions.

At present, the solutions proposed for limiting slime formation employ chemical or, alternatively, biocidal disinfectants. These are generally organochlorine- and organobromine-based chemicals which effectively inhibit the growth of the contaminant flora.

However, by virtue of their chemical nature, these compounds are not entirely satisfactory.

For example, they are highly toxic and nonbiodegradable.

Their release, even partial, into the environment also presents serious ecological difficulties, and, more especially, creates a problem of purification of the contaminated water.

Finally, to attain effective inhibition of the bacterial flora, it is necessary to employ several biocides alternately, as well as increasingly greater amounts or doses thereof. It is apparent that the repeated introduction of such larger amounts aggravates the problem of pollution.

Consequently, the use of biocides for the treatment of bacterial flora is today highly suspect from an ecological standpoint and means for avoiding such use is a more than desirable goal.

SUMMARY OF THE INVENTION

Accordingly, a major object of the present invention is the provision of substitute disinfectants for the biocides that exhibit comparable efficacy therewith, but which, in contrast thereto, do not adversely affect the environment.

Briefly, the present invention features a process for regulating the growth and propagation of the microbial and/or bacterial flora that exist in the water circuits and feedstreams in the papermaking industry, whereby such waters are treated with an effective disinfectant amount of bacteria of the genus *Staphylococcus* or *Acinetobacter*.

DETAILED DESCRIPTION OF PREFERRED EMBODIMENTS OF THE INVENTION

More particularly according to the present invention, by "disinfectant" is intended an agent suited for controlling, and more characteristically for terminating the growth of the undesirable biological flora that develop in aqueous papermaking circuits and process streams.

By "microbial and/or bacterial" flora are intended the flora that contaminate the water circuits and process streams in the papermaking industry; these are typically yeasts, molds and enterobacteria.

Particularly representative microorganisms of these flora are molds of the genus *Penicillium*, *Mucor* or *Aspergillus*, yeasts such as *Candida* and *Rhodotorula*, aerobic bacteria of the genus *Pseudomonas*, *Enterobacter* or *Bacillus*, and *Clostridia* as anaerobic bacteria.

The diversity of these microorganisms traditionally necessitates the simultaneous use of a plurality of biocides.

Unexpectedly, it has now been determined that the bacteria selected according to the invention inhibit the growth of all of these contaminant flora effectively. They are active with respect to all of the aforementioned microorganisms and in general do not necessitate treatment with any additional biocide. No slime formation is observed in their presence, and completely problem-free papermaking is assured.

The bacteria employed according to the invention are, more especially, bacteria of the genus *Staphylococcus* or *Acinetobacter*, and preferably are bacteria of the species *Staphylococcus carnosus*, and more preferably that marketed under the trademark M 72 by TEXEL, and the characteristics of which are reported in the example below, or one of the mutants or recombinants thereof.

The bacteria, notably those of the species *Staphylococcus carnosus*, are non-corrosive and completely safe. The bacterium M 72 is, in particular, already employed in the food industry. Consequently, their partial release into the environment does not present any ecological problems.

The strains according to the invention are, in addition, preferably temperature-sensitive strains, namely, those which are destroyed simply by heating. This characteristic presents a further advantage in comparison to biocides. At the end of the production line, the residual bacteria remaining in the wet sheet of paper will be destroyed on drying this sheet prior to the winding sequence. Biocides, on the other hand, may remain in trace amounts in the final paper.

The bacteria according to the invention may be introduced at any point along the papermaking line. However, for reasons of convenience, they are preferably introduced at the beginning of the production line.

The amount of bacteria introduced into the papermaking circuit is naturally dependent on the pH, the temperature, the volume of water in circulation and the amount of paper treated in such circuit. Generally, it ranges from $1 \times 10^{13}$ bacteria per metric ton of paper to be treated. In a preferred embodiment of the invention, the amount of bacteria ranges from $1 \times 10^{12}$ to $10 \times 10^{12}$ bacteria per metric ton of paper.

A daily inoculation of the process water used with bacteria according to the invention proves sufficient for effective inhibition of the growth of the bacterial flora. However, this inoculation may of course be repeated once or twice.

The bacteria according to the invention elicit, in addition, no adverse effect on the performance of other additives traditionally employed in the papermaking process, of the dispersant, antifoam or retention agent type, for example.

The bacteria may optionally be combined with other disinfectant agents, again with the proviso that the latter elicit no adverse effect with respect thereto.

The analysis of samples of water from a paper production line treated according to the process of the invention confirms the absence of growth of the usual flora.

Without wishing to be bound by or to any particular theory, the surprising and unexpected efficacy of the bacteria according to the invention with respect to such bacterial flora is likely explained by the following:

The microorganisms present in the water circuits are exposed to optimal growth conditions as a result of favorable pH, temperature and oxygenation conditions and of a surplus of organic and inorganic nutrients permanently present in the system.

With traditional biocides, the biological equilibrium of the system is shifted, reducing the level of bacteria. The growth of new bacteria is not prevented.

In the case of the process according to the present invention, the growth of the bacteria is the parameter that is disturbed. The bacteria according to the invention deprive the contaminant bacteria of their nutrients. Growth of new contaminant bacteria no longer occurs, which has the immediate effect of completely stopping slime formation.

The bacteria according to the invention produce, in addition, nitratoreductase. This enzyme reduces nitrates to nitrites which, for their part, elicit bacteriostatic activity. Since the water in the papermaking industry is very rich in nitrates, it is likely that this bacteriostatic activity complements the aforesaid deprivatory activity of the subject bacteria.

Finally, any bacterium can produce bactericides which will also contribute to the removal of a fraction of the contaminant flora.

Other than its disinfectant efficacy and its compatibility with the environment, the process according to the invention affords added advantages of an economic and technical nature.

The use of the bacteria according to the invention makes it possible to effectively eliminate the breaks, holes, spots and other production problems usually caused by slimes. This results in an increased profitability of the production process.

Finally, the improvement in the bacteriological quality of the water, the reduction in toxicity, the elimination of foul odors and the better functioning of the papermaking machine which are attributed to the process according to the invention also contribute to an improvement in the working conditions for personnel in the papermaking industries.

In order to further illustrate the present invention and the advantages thereof, the following specific example is given, it being understood that same is intended only as illustrative and in nowise limitative.

EXAMPLE

The bacteria employed as the disinfectant were bacteria marketed by TEXEL as M 72.

Such microorganism, more specifically, was a *Staphylococcus carnosus* having the following characteristics:

Morphological Characteristics

Cocci occurring alone, in pairs, in tetrads or irregular masses.

Physiological Characteristics

Gram-positive,
Asporogenous,
Non-mobile,
Catalase-positive,
Homofermentative (no carbon dioxide production),
Growth temperature: 12°–42° C.,
Optimal growth temperature: 25°–32° C.

| Biochemical characteristics: | | | |
|---|---|---|---|
| Symbols: positive reaction + negative reaction − | | | |
| L-Arabionose | − | Xylitol | − |
| D-Cellobiose | − | N-Acetyl-glucosamine | + |
| D-Fucose | − | Methyl α-D-glucoside | − |
| β-D-Fructose | + | Acetyl methyl carbinol | + |
| D-Galactose | − | Salicin | − |
| D-Glucose | + | Nitrate reduction | + |
| α-Lactose | + | Alkaline phosphatase | + |
| Maltose | − | Arginine dihydrolase | + |
| D-Mannose | + | Urease | − |
| D-Melibiose | − | Coagulase | − |
| D-Melezitose | − | DNase | − |
| D-Raffinose | − | Lysostaphin resistance | − |
| Sucrose | − | Lysozyme resistance | + |
| D-Trehalose | − | | |
| D-Xylose | − | | |
| D-Mannitol | + | | |

The activity of these bacteria was determined in the papermaking industry on a traditional production circuit/line.

The bacteria were introduced, once per day, into the machine tank or pulper at an inoculation level on the order of $5 \times 10^{12}$ bacteria per metric ton of paper treated. In the present example, paper production was assessed at from 25 to 30 metric tons per day. Water samples were withdrawn daily at several points along the principal and secondary circuit, and their mold, bacterial and yeast concentration were determined by standard assay methods using appropriate culture media.

Medium for Testing for Coliforms (a) lactose broth with bile and brilliant green,
(b) lactose agar with deoxycholate.

Medium for Testing for Enterococci

D-coccosel agar.

Medium for Testing for Pathogenic Staphylococci

Baird-Parker agar with tellurite.

Medium for Testing for Sulfite-Reducing Anaerobes—Clostridium

M-L (meat-liver) agar.

Medium for Testing for Contaminant Molds/Yeasts

M-E (malt extract) agar.

Medium for Testing for Total Aerobic Mesophilic Flora milk-enriched PCA agar.

The results are reported in the Table below.

In this Table, at T equals zero, the initial concentration of microbial flora in the water is indicated. The bacteria according to the invention were introduced daily from T equals 1.

A decrease in the concentration of microbial flora to a value close to zero was very rapidly observed. These measurements confirmed the efficacy of the process according to the invention. From T equals 28, which corresponded to the cessation of the supply of bacteria to the water, a very rapid recrudescence of the microbial flora was noted.

TABLE

| | CONCENTRATION ($\times$ 1,000): | | |
|---|---|---|---|
| T (days) | Entero-bacteria | Molds | Yeast |
| T0 | 1,180 | 860 | 1,020 |
| 1 d. (start of the treatment) | | | |
| 2 d. | 950 | 580 | 780 |
| 3 d. | n.d. | 300 | n.d. |
| 4 d. | 580 | 100 | 220 |
| 5 d. | 150 | <70 | 160 |
| 6 d. | 100 | 50 | 100 |
| 7 d. | 50 | <20 | 50 |
| 8 d. | <0.01 | <0.01 | <0.01 |
| 27 d. (cessation of the treatment) | | | |
| 28 d. | 380 | 200 | 580 |
| 29 d. | 740 | 420 | 780 |
| 30 d. | 1,100 | 500 | 700 |

*n.d. = not determined

While the invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A process for regulating the growth of the microbial/bacterial flora existing in an aqueous papermaking circuit/process stream, comprising introducing into such circuit/process stream an effective disinfectant amount of bacteria of the species Staphylococcus carnosus.

2. The process as defined by claim 1, said bacteria of the species Staphylococcus carnosus having the designation M 72.

3. The process as defined by claim 1, comprising introducing from $1 \times 10^{10}$ to $10 \times 10^{13}$ disinfectant bacteria per metric ton of paper produced.

4. The process as defined by claim 3, comprising introducing from $1 \times 10^{12}$ to $10 \times 10^{12}$ disinfectant bacteria per metric ton of paper produced.

5. The process as defined by claim 1, comprising introducing said disinfectant bacteria at least once a day into such circuit/process stream.

6. The process as defined by claim 1, comprising also introducing at least one different disinfectant into such circuit/process stream.

* * * * *